US00PP08935P

United States Patent [19]

VandenBerg

[11] Patent Number: Plant 8,935

[45] Date of Patent: Oct. 11, 1994

[54] CHRYSANTHEMUM PLANT NAMED EFFECT

[75] Inventor: Cornelius P. VandenBerg, Salinas, Calif.

[73] Assignee: Yoder Brothers, Inc., Barberton, Ohio

[21] Appl. No.: 125,240

[22] Filed: Sep. 23, 1993

[51] Int. Cl.[5] ..... A01H 5/00

[52] U.S. Cl. ..... Plt./74.1

[58] Field of Search ..... Plt. 74.1, 82.4

*Primary Examiner*—Howard J. Locker

*Attorney, Agent, or Firm*—Foley & Lardner

[57] ABSTRACT

A Chrysanthemum plant named Effect particularly characterized by its flat capitulum form; anemone capitulum type; purple ray floret color, with fresh green to yellow-green anemone cushion; diameter across face of capitulum of 70 to 76 mm when fully opened, when grown as a single stem spray cut mum; photoperiodic flowering response to short days of 49 to 54 days when grown in Salinas, Calif.; plant height of 71 to 86 cm with 11 long days after planting rooted cuttings prior to start of short days when grown as a single stem cut mum, with no growth regulator applications; peduncle length at flowering time of the first lateral after removing the apical bud is 8 to 10 cm; peduncle length of the fourth lateral is 10 to 15 cm; and recommended as a single stem spray cut mum.

3 Drawing Sheets

The present invention comprises a new and distinct cultivar of Chrysanthemum, botanically known as *Dendranthema grandiflora,* and referred to by the cultivar name Effect.

Effect, identified as 2602 (88-042003), was originated from a cross made by Cornelis P. VandenBerg in a controlled breeding program in Salinas, Calif., in 1986.

The female parent of Effect was an unnamed seedling identified as 1443 (83-754009), and described as a flat spooned anemone spray cut mum with a pink ray floret color; a flowering response to short days of 53 to 62 days under normal conditions in Salinas, Calif.; a plant height of 69 to 84 cm with 14 to 15 long days after planting rooted cuttings prior to start of short days; peduncle length of the first lateral after removing the apical bud of 8 to 10 cm, and peduncle length of the fourth lateral of 13 to 18 cm when grown in Salinas. Diameter of capitulum was not recorded. The female parent was discarded in June 1988.

The male parent of Effect was an unnamed seedling, identified as 6617 (84-165016) and described as a flat daisy spray cut mum with a red-bronze ray floret color; a flowering response to short days of 52 to 63 days under normal conditions in Salinas, Calif.; a plant height of 61 to 91 cm with 6 to 14 long days after planting rooted cuttings prior to start of short days; peduncle length of the first lateral after removing the apical bud of 5 to 10 cm, and peduncle length of the fourth lateral of 10 to 15 cm when grown in Salinas; and diameter of capitulum of 44 to 51 mm. The male parent was discarded on Apr. 15, 1988.

Effect was discovered and selected as one flowering plant within the progeny of the stated cross by Cornelius P. VandenBerg in August 1988, in a controlled environment in Salinas, Calif.

The first act of asexual reproduction of Effect was accomplished when vegetative cuttings were taken from the initial selection in November 1988 in a controlled environment in Salinas, Calif., by technicians working under supervision of Cornelis P. VandenBerg.

Horticultural examination of controlled flowerings of successive plantings has shown that the unique combination of characteristics as herein disclosed for Effect are firmly fixed and are retained through successive generations of asexual reproduction.

Effect has not been observed under all possible environmental conditions. The phenotype may vary significantly with variations in environment such as temperature, light intensity and daylength, without, however, any variation in genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of Effect, which, in combination, distinguish this Chrysanthemum as a new and distinct cultivar:

1. Flat capitulum form.
2. Anemone capitulum type.
3. Purple ray floret color, with fresh green to yellow-green anemone cushion.
4. Diameter across face of capitulum of 70 to 76 mm when fully opened, when grown as a single stem spray cut mum.
5. Photoperiodic flowering response to short days of 49 to 54 days when grown in Salinas, Calif.
6. Plant height of 71 to 86 cm with 11 long days after planting rooted cuttings prior to start of short days when grown as a single stem cut mum, with no growth regulator applications.
7. Peduncle length at flowering time of the first lateral after removing the apical bud is 8 to 10 cm; peduncle length of the fourth lateral is 10 to 15 cm.
8. Recommended as a single stem spray cut mum.

The accompanying photographic drawings show typical inflorescence and leaf characteristics of Effect, with the colors being as nearly true as possible with illustrations of this type. Sheet 1 is a color photograph of a side view of Effect grown as a single stem cut mum. Sheet 2 is a black and white photograph of three views of the inflorescence of Effect. Sheet 3 is a black and white photograph showing the upper and under sides of the leaves of Effect at 3 stages of development (mature, intermediate and immature). In sheets 2 and 3 a measuring tape in centimeters has been added.

Of the commercial cultivars known to the inventor, the most similar in comparison to Effect is the cultivar Lambada, disclosed in U.S. Plant Pat. No. 8,466. Reference is made to attached Chart A, which compares certain characteristics of Effect to the same characteristics of Lambada.

Similar or comparable traits are capitulum form and type, diameter across face of capitulum, flowering response to short days, plant height, peduncle length and spray formation. Effect has a darker ray floret color than Lambada, and a darker green anemone cushion when opening when compared with Lambada.

In the following description color references are made to the Royal Horticultural Society Colour Chart. The color values were determined on plant material grown as a single stem spray cut mum in Salinas, Calif., on Jun. 29, 1992.

Classification:

*Botanical.*—*Dendranthema grandiflora* cv Effect.

*Commercial.*—Anemone spray cut mum.

INFLORESCENCE

A. Capitulum:

*Form.*—Flat.

*Type.*—Anemone.

*Diameter across face.*—70 to 76 mm when fully opened.

B. Corolla of ray florets:

*Color (general tonality from a distance of three meters).*—Purple.

*Color (upper surface).*—75A, fading to 75B–75C.

*Color (under surface).*—75B to 75C.

*Shape.*—Straight, base concave, mature petal tips convex. Cross section straight, slightly ribbed.

C. Corolla of disc florets:

*Color (mature).*—154D, slightly overlaid with 144A.

*Color (immature).*—144B.

D. Reproductive organs:

*Androecium.*—Present on disc florets only; no pollen.

*Gynoecium.*—Present on both ray and disc florets.

PLANT

A. General appearance:

*Height.*—71 to 86 cm when grown in Salinas with 11 long days prior to start of short days.

B. Foliage:

*Color (upper surface).*—147A.

*Color (under surface).*—147B.

*Shape.*—See photograph.

CHART A

COMPARISON OF EFFECT AND LAMBADA

| CHARACTERISTIC | EFFECT | LAMBADA |
|---|---|---|
| Ray floret color | Purple 75A | Soft pink 75B |
| Disc floret color | 154D, overlaid with 144A | Yellow, overlaid with 145A |
| Capitulum form and type | Flat anemone | Flat anemone |
| Diameter across face of capitulum | 70 to 76 mm | 67 to 83 mm |
| Flowering response | 49 to 54 days | 47 to 59 days |
| Plant height | 71 to 86 | 71 to 87 cm |
| Peduncle length: | | |
| 1st lateral | 8 to 15 cm | 8 to 15 cm |
| 4th lateral | 10 to 15 cm | 10 to 20 cm |
| Spray formation | Terminal | Terminal |

COMPARISONS MADE OF PLANTS GROWN AS SINGLE STEM SPRAY CUT MUMS IN SALINAS, CALIFORNIA

I claim:

1. A new and distinct Chrysanthemum plant named Effect, as described and illustrated.

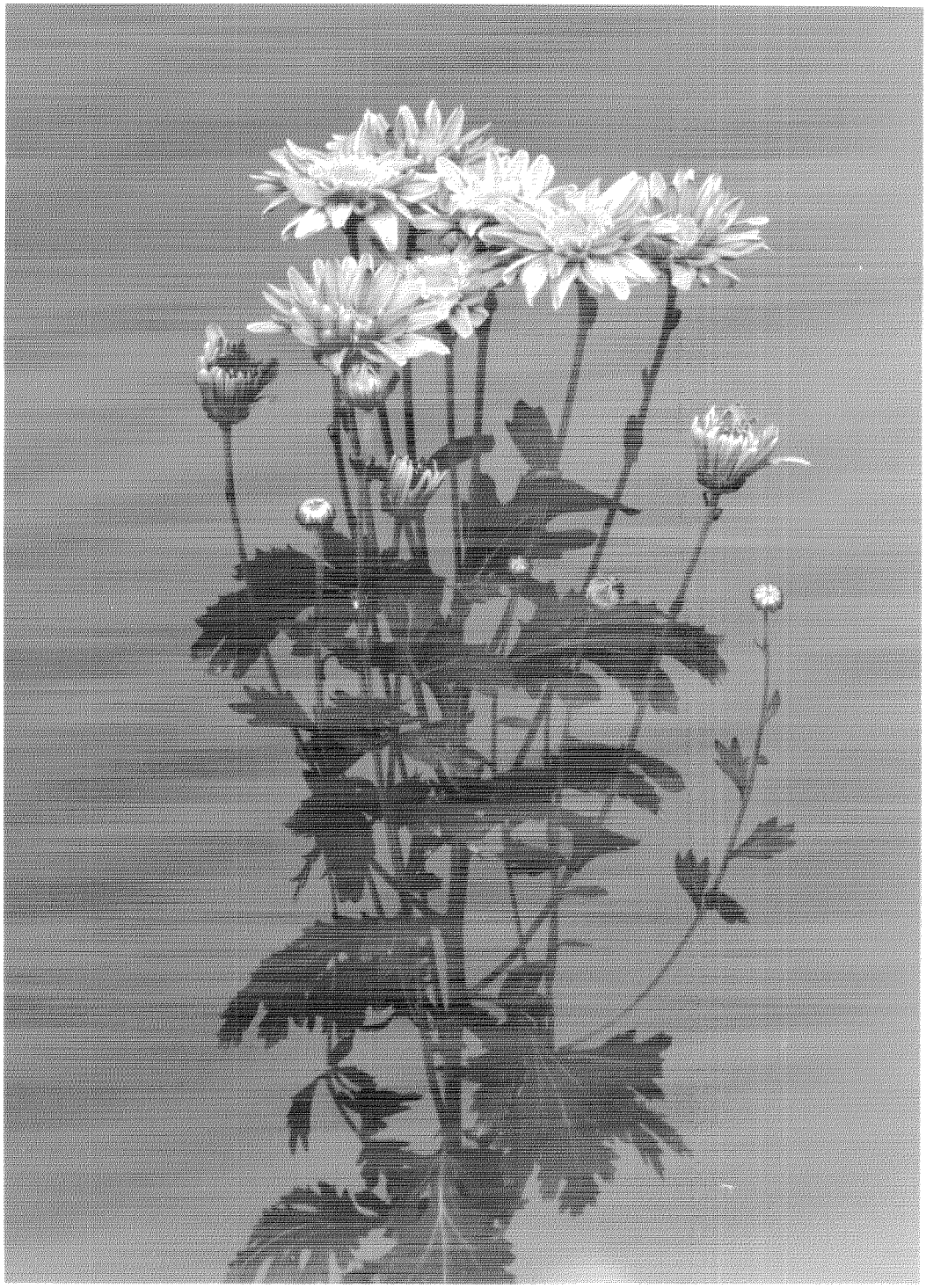

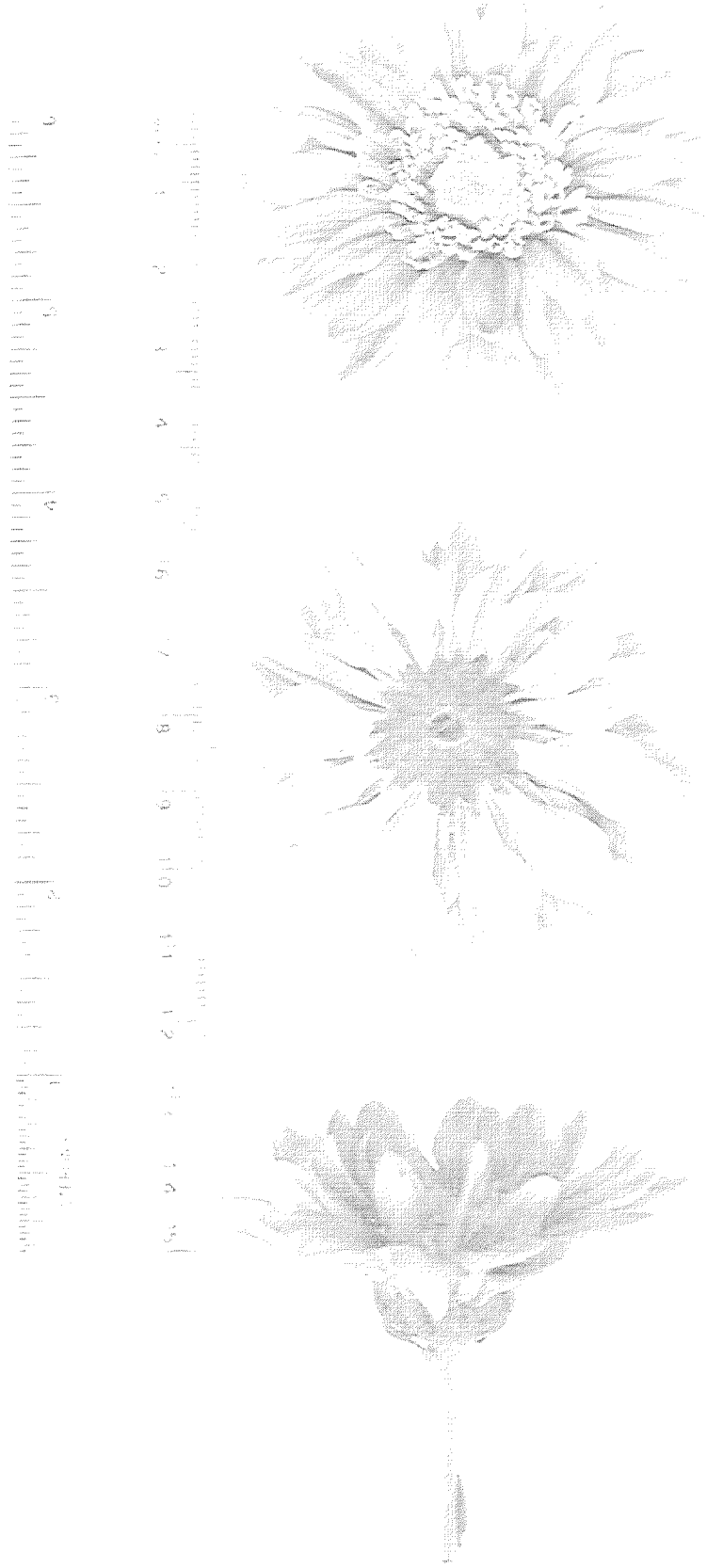

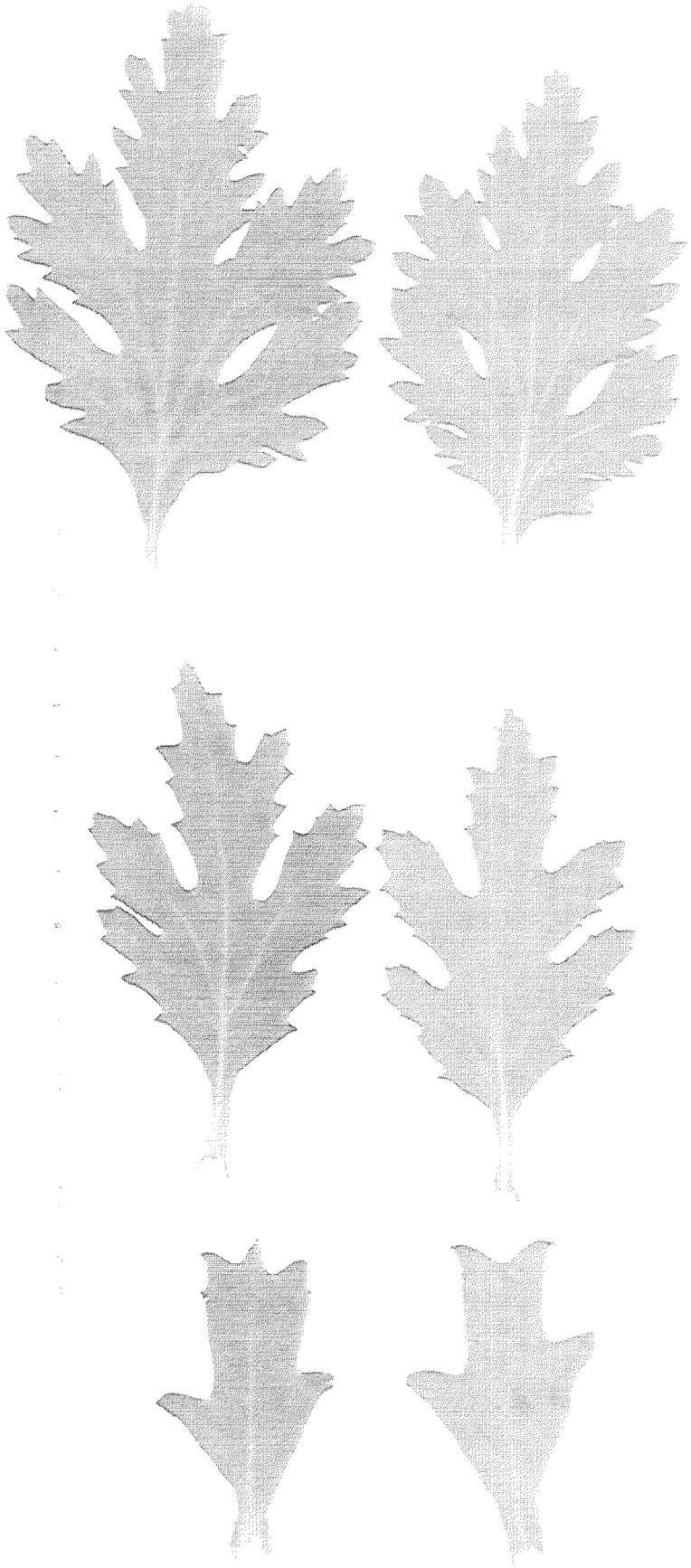

* * * * *